United States Patent [19]

Yamada et al.

[11] Patent Number: 5,372,994
[45] Date of Patent: Dec. 13, 1994

[54] FRAGRANT COMPOSITION

[75] Inventors: Toshiro Yamada, Fujisawa; Hiroshi Fujisawa, Kawasaki; Hideyuki Tanaka, Yokohama, all of Japan

[73] Assignee: Nippon Zeon Co., Ltd., Tokyo, Japan

[21] Appl. No.: 3,934

[22] Filed: Jan. 21, 1993

Related U.S. Application Data

[63] Continuation of Ser. No. 853,870, Mar. 20, 1992, Pat. No. 5,235,110, which is a continuation of Ser. No. 526,142, May 22, 1990, abandoned.

[30] Foreign Application Priority Data

| May 23, 1989 | [JP] | Japan | 1-129919 |
| Aug. 25, 1989 | [JP] | Japan | 1-219596 |
| Mar. 29, 1990 | [JP] | Japan | 2-082841 |

[51] Int. Cl.$^5$ .............................................. A61K 7/46
[52] U.S. Cl. .................................................... 512/8
[58] Field of Search ........................................ 512/8

[56] References Cited

U.S. PATENT DOCUMENTS

| 3,158,644 | 11/1964 | Demole et al. | 512/8 |
| 3,288,833 | 11/1966 | Demole | 512/8 |
| 3,970,682 | 7/1976 | Plattier et al. | 512/8 |
| 3,978,108 | 8/1976 | Teisseire et al. | 512/8 |
| 4,016,109 | 4/1977 | Cohen | 512/8 |
| 4,260,512 | 4/1981 | Mookherjee | 512/8 |

FOREIGN PATENT DOCUMENTS

| 0062979 | 10/1982 | European Pat. Off. | |
| 1467516 | 1/1969 | Germany | 512/8 |
| 2162820 | 7/1972 | Germany | |
| 2260447 | 6/1973 | Germany | |
| 3037 | 1/1977 | Japan | |

OTHER PUBLICATIONS

Chemical Abstracts, vol. 84, No. 17, Apr. 26, 1976, p. 496, Abs. No. 121298w, Columbus, Ohio, U.S. of JP 75-131952: Oct. 18, 1975.
Japanese Patent Abstract, vol. 11, No. 297 (C-448) [2744] Sep. 25, 1987 of JP 62-87555, Apr. 22, 1987.
Proceedings of 30th Symposium of Terpenes, Essential Oils, and Aromatics (1988).
Proceedings of 32th Symposium of Terpenes, Essential Oils, and Aromatics (1990).
Kalish, D+Cl., pp. 162-163 (1966).
Koryo Sangyo Shinbun (Perfume Industry News) (1985).
Proceedings of Annual Meeting and 29th Symposium of the Japanese Society of Plant Physiologists (1985).
Proceedings of 29th Symposium of Terpenes, Essential Oils, and Aromatics 1987.
Plant Physiol. 66, 246-249 (1980).
Agric. Biol. Chem., 49 (3), 769-772, 1985.
Agric. Biol. Chem., 51 (4), 1129-1133, 1987.

*Primary Examiner*—James H. Reamer
*Attorney, Agent, or Firm*—Nikaido Marmelstein Murray & Oram

[57] ABSTRACT

The invention discloses a process for preparing a 2,3-di-substituted cyclopentanone mixture containing an enriched cis-2,3-di-substituted cyclopentanone which comprises heating a trans-2,3-di-substituted cyclopentanone in the presence of 100 ppm or less (weight basis) of a metal carbonate based on the cyclopentanone. The invention also discloses a fragrant composition comprising 20 to 50 wt % of 2,3-di-substituted cis-methyl (dihydro)jasmonates and 80 to 50 wt % of 2,3-di-substituted (dihydro) trans-methyl (dihydro)jasmonates. The fragrant composition has jasmine flower-like fragrance.

5 Claims, No Drawings

FRAGRANT COMPOSITION

This is a continuation of application Ser. No. 07/853,870 filed Mar. 20, 1992 now U.S. Pat. No. 5,235,110 which is a continuation of application Ser. No. 07/526,142 filed May 22, 1990 (now abandoned).

BACKGROUND OF THE INVENTION

1. Field of the Invention

The present invention relates to a process for preparing a 2,3-di-substituted cyclopentanone mixture and a fragrant composition comprising the mixture which has excellent jasmine flower-like fragrance as well as a diluted fragrant composition.

2. Related Art Statement 2,3-Di-substituted cyclopentanones represented by methyl jasmonate and methyl dihydrojasmonate are chemical substances useful in the fields of fragrance, drugs, chemicals and the like.

Such 2,3-di-substituted cyolopentanonee involve steric isomers of cis-isomer and trans-isomer, as shown by general formulae (I) through (IV) described below. Recent studies reveal that the ois-isomer is excellent in organoleptic evaluation and physiological activity, as compared to the trans-isomer.

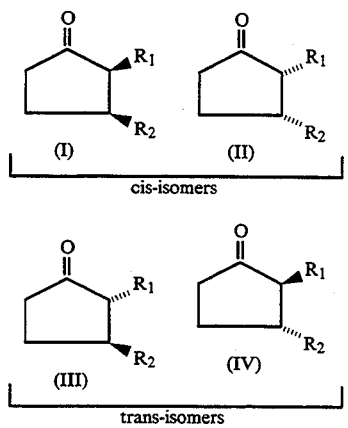

(wherein $R_1$ represents a hydrocarbon residue and $R_2$ represents a hydrocarbon residue which may optionally have a substituent).

In the case of, for example, methyl jasmonate, it is reported that the essence of its fragrance is present in the cis-isomer (Agricultural and Biological Chemistry, 49, 769, 1985) and that the cis-isomer is more active in the physiological activity on plants than the trans-isomer or a mixture of the cis-isomer and the trans-isomer (Preprints of the Plant Physiological Association, page 347, 1989; Plant Physiology, 66, 246, 1980, etc.).

Based on these findings, synthesis of and research on cis-2,3-di-substituted cyclopentanones have been extensively made. The syntheses of, for example, methyl jasmonate or methyl dihydrojasmonate are reported in Preprints of the 29th Discussions on Fragrance, Terpene and Essential oil Chemistry, page 222, 1985; Preprints of the 30th Discussions, page 101, 1986; Preprints of the 32nd Discussions, page 132, 1988; etc. However, these processes fail to efficiently produce the cis-isomer. In addition, the processes encounter practical problems since many reaction steps are involved and expensive reactants are used.

On the other hand, it is known that when the cis-isomer is compared to the trans-isomer, the trans-isomer is generally advantageous in view of equilibrium. It was thus studied to obtain the cis-isomer efficiently by converting the trans-isomer into the cis-isomer and recently, a process for treating methyl jasmonate with p-toluenesulfonic acid in the presence of a solvent was reported (Fragrance Industry News, No. 247, Apr. 15, 1988, page 6). According to the process, however, the yield of the cis-isomer is as low as about 5%. In addition, there is a fear that side reactions tend to occur.

As described above, methyl jasmonate [formula (I-a) below] and methyl dihydrojasmonate [formula (II-a) below] have jasmine flower-like fragrance and are useful compounds as perfume or cosmetics and as fragrance formulated in food.

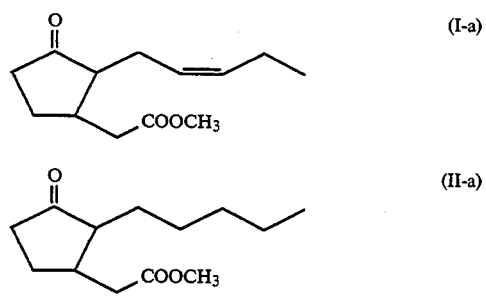

These compounds have two chiral centers (two asymmetric carbons in the 5-membered ring) so that 4 optical isomers are present, respectively.

For example, methyl jasmonate has 4 optical isomers as shown by formulae (III-a) through (VI-a) described below. As stated above, it is revealed that the essence of fragrance is present in the (+) cis-isomer shown by formula (III-a) below, among these isomers.

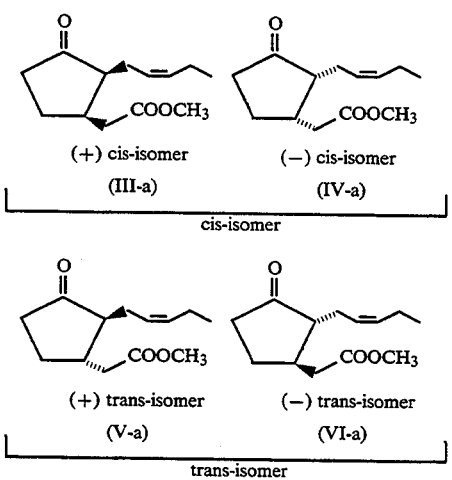

Therefore, synthesis of and investigations on the (+) cis-isomer have been extensively made as described above, which are reported in, for example, Agricultural Biological Chemistry, 5, 1129, 1987. However, these processes involve many reaction steps and use of expensive reactants so that production costs are high and the processes are not economical.

An economical process has been developed but the reaction product is a mixture of the cis-isomer and the trans-isomer shown by the above formulae and also takes a racemic form. In addition, the trans-isomer is produced in an amount larger than the cis-isomer because of its equilibrium advantageously shifted toward the trans-isomer so that the ratio of the cis-isomer to the trans-isomer contained in the reaction product is approximately 5:95 (weight basis), indicating that the trans-isomer is greatly predominant. Thus, the process involves a defect that the intensity of fragrance is not very strong.

SUMMARY OF THE INVENTION

As a result of extensive investigations to solve the foregoing defects, the present inventors have found that by heating the trans-isomer of 2,3-di-substituted cyclopentanones in the presence of a metal carbonate, the cis-isomer-enriched cyclopentanones can be obtained in a good yield and also by delicately controlling the amount of the metal carbonate used in this case, the cis-isomer-enriched cyclopentanones can be obtained efficiently. Based on the findings, the present invention has come to be accomplished in its first aspect.

Therefore, according to the first aspect of the present invention, there is provided, as a first embodiment, a process for preparing a 2,3-di-substituted cyclopentanone mixture containing a cis-2,3-di-substituted cyclopentanone which comprises heating a trans-2,3-di-substituted cyclopentanone in the presence of a metal carbonate. There is also provided, as a second embodiment, a process for preparing a 2,3-di-substituted cyclopentanone mixture containing an enriched cis-2,3-di-substituted cyclopentanone which comprises heating the cyclopentanone in the presence of 100 ppm or less (weight basis) of a metal carbonate salt and then distilling the mixture.

The present inventors have continued further extensive investigations to efficiently obtain materials having an excellent fragrant property utilizing the mixture prepared by the above process. As a result, it has been found that the content of the cis-isomer can be increased further by concentrating by means of distillation under specific conditions and when the content of the cis-isomer becomes 20% or more in the total amount of cis- and trans-isomers. The composition exerts a much superior fragrant intensity than the composition containing 10% of the cis-isomer in the total amount of cis- and trans-isomers and the resulting composition is sufficiently satisfactory as a fragrant composition. In this specification, the above-mentioned step is sometimes referred to as concentration. It has also been found that a fragrance composition diluted with a solvent such as ethanol which is volatile et normal temperature shows an unexpectedly remarkable fragrance intensity comparable to a diluted fragrance composition prepared from highly purified cis-isomere and such en intensity can not be attained by only adjusting the absolute content of the cis-isomers to the identical level at the time of preparing the diluted fragrance composition unless said undiluted fragrance composition contains 20% to 50% of the cis-isomers therein. Based on these findings, the present invention has come to be accomplished in its second aspect.

Therefore, according to the second aspect of the present invention, there is provided a fragrant composition comprising the cis-isomer (racemate) and trans-isomer (racemate) of methyl jasmonate or methyl dihydrojasmonate, in which the cis-isomer and the trans-isomer are contained in 20 to 50% and 80 to 50% (weight basis), respectively.

The fragrant composition may also be used by diluting with a volatile solvent without changing the relative concentration between iso- and trans-isomers at normal temperature.

DETAILED DESCRIPTION OF PREFERRED EMBODIMENTS

The raw material used in the first aspect of the present invention is trans-2,3-di-substituted cyclopentanones represented by general formulae (III) and (IV) above. Indeed, a mixture of cis-and-trans cyclopentanones can be used as far as the concentration of the cis-isomers is lower than its intended concentration. In the formulae, $R_1$ represents a hydrocarbon residue such as an alkyl group, e.g., methyl, ethyl, propyl, butyl, pentyl, hexyl, nonyl, etc.; an alkenyl group, e.g., vinyl, propenyl, butenyl, pentenyl, hexenyl, etc.; an alkynyl group, e.g., ethynyl, propynyl, butynyl, pentynyl, hexynyl, etc.

Turning to $R_2$, $R_2$ represents the same hydrocarbon residue as exemplified for $R_1$ and may further be a hydrocarbon residue having a substituent thereon such as an alkoxycarbonyl group, an alkoxyalkyl group, an alkoxycarbonylalkyl group, etc.

In the present invention, the metal carbonate is used as a catalyst. Specific examples of the metal carbonate are alkali metal salts such as sodium carbonate, potassium carbonate, lithium carbonate, sodium hydrogencarbonate, potassium hydrogencarbonate, etc.; alkaline earth metal salts such as calcium carbonate, magnesium carbonate, etc.; transition metal salts such as copper carbonate, nickel carbonate, etc. Of these, alkali metal salts ace preferred.

An amount of the metal carbonate is not primarily limited since the amount may-vary depending upon kind of the metal carbonate, reaction conditions, etc. However, the amount is generally 10 ppb or more (weight basis), preferably less 100 ppb or more, based on the starting trans-2,3-di-substituted cyclopentanone. The upper limit of the amount is not particularly restricted. However, the catalyst which does not dissolve at the reaction temperature merely remains in the system as the slurry but does not contribute to the reaction. Thus, the amount is generally set forth within such a range that the amount does not exceed the solubility of the metal carbonate.

In the first aspect of the present invention, where the distillation is carried out as a post-treatment alter completion of the reaction, it is preferred to control delicately the amount of the metal carbonate metal within a specified range. The upper limit is set to 100 ppm or less (weight basis), preferably 10 ppm or less, more preferably 1 ppm or less, based on the weight of the trans-2,3-di-substituted cyolopentanone. For controlling to such a trace amount, there are, for example, a method in which the metal carbonate is dissolved at a dissolution temperature corresponding to the desired concentration and then insoluble catalyst is removed by filtration; a method in which a previously prepared dilution is used; etc. The equilibrium between the cis-isomers and the trans-isomers is generally shifted advantageously toward the cis-isomers generally at high temperatures. However, the operation for distillation should be carried out at a temperature lower than the temperature for the equilibrium, for purposes of preventing generation of unpleasant odor and coloration and enhancing the efficiency of distillation. In this case, however, when the upper limit of the metal carbonate exceeds the range set forth above, namely, 100 ppm, there is a defect that the equilibriun shifts from the cis-isomers to the trans-isomers upon distillation and the yield of the cis-isomers decreases.

The reaction of the present invention proceeds by heating the raw material in the presence of the metal carbonate. A reaction temperature is generally between 60° and 300° C., preferably between 100° and 250° C., more preferably between 110° and 22020 C. A reaction time is generally 5 minutes to 36 hours.

Upon the reaction, a diluent may also be present in the system. Specific examples of the diluent include nitriles such as acetonitrile, benzonitrile, etc.; amides such as dimethylformamide, dimethylacetamide, etc.; ethers such as tetrahydrofuran, dioxan, etc.; ketones such as acetone, methyl ethyl ketone, etc.; esters such as methyl acetate, ethyl acetate, etc.; alcohols such as ethanol, propanol, etc.; sulfoxides such as dimethylsulfoxide, diethylsulfoxide, etc.; hydrocarbons such as n-hexane, benzene, toluene, etc.

After completion of the reaction, the reaction mixture is post-treated in a conventional manner to give a product having a good quality. The post treatment includes, for example, distillation, extraction with a solvent, washing with water, etc. From an operational viewpoint, distillation is preferred. Where distillation is carried out, it is necessary to delicately control the amount of the metal carbonate, for the reasons described above. Conditions for the distillation are appropriately chosen depending upon kind of the reaction product but it is preferred to perform the distillation at a low temperature because of the reasons described above. The distillation is performed generally at a boiling point of 170° C. or below, preferably below 160° C., more preferably below 150° C.; at a liquid temperature of 250° C. or below, preferably below 220° C., more preferably below 200° C.

The thus obtained 2,3-di-substituted cyclopentanone is a mixture containing the enriched cis-2,3-di-substituted cyclopentanones represented by general formulae (I) and (II). In the reaction in accordance With the first aspect of the present invention, the side chain at the 2-position of the cyclopentanone is selectively reversed so that the structure of the cis-isomers in the product is different depending upon the structure of the raw material. That is, the cis-isomer of general formula (I) is obtained from the trans-isomer of general formula (III) and, the cis-isomer of general formula (II) is obtained from the trans-isomer of general formula (IV).

Therefore, according to the first aspect of the present invention, the cis-isomer enriched 2,3-di-substituted cyclopentanone can be obtained in a high yield, as compared to the prior art.

The cis-isomers and trans-isomers of methyl jasmonate or methyl dihydrojasmonate in accordance with the second aspect of the present invention take racemic forms. In the case of, for example, methyl jasmonate, the cis- and trans-isomers are composed of equal amounts of (+) isomer and (−) isomer, respectively, as shown by the above formulae (III-a) through (VI-a).

As described above, the fragrant composition in accordance with the second aspect of the present invention comprises a mixture composed of the cis-isomers and the trans-isomers which take the racemic forms, respectively. Its constitutional ratio is 20 to 50% of the cis-isomers and 80 to 50% of the trans-isomers, on the basis of weight.

The mixture of such a composition can be obtained, utilizing the process in accordance with the first aspect of the present invention. The process is described with reference to methyl jasmonate also but in the case of methyl dihydrojasmonate, the mixture can be obtained in a similar manner. Firstly, methyl jasmonate is heat-treated in the presence of a catalyst for isomerization, for example, an alkali such as the metal carbonate, etc., or an acid such as acidic ion exchange resin, etc., by the process in accordance with the first aspect of the present invention, whereby a part of the trans-isomers is converted into the cis-isomers. Then, the catalyst is removed by distillation or the like for purification. By this treatment, the content of the cis-isomers generally becomes about 10%. Then, the thus obtained mixture is concentrated by distillation, utilizing the difference in boiling point between the cis-isomers and the trans-isomers to remove the trans-isomers. Thus, the content of the cis-isomers is increased to 20 to 50%. Conditions for the distillation to remove the trans-isomers are generally at a boiling point of 90° C. to 180° C. under a pressure of 0.01 mmHg to 25 mmHg, preferably at a boiling point of 100° C. to 130° C. under a pressure of 0.03 mmHg to 2 mmHg. Such distillation is generally carried out using a stainless fractionating tower or a fractionating tower packed with a stainless filler. Previous washing of a fractionating tower with hot water, steam, etc., can prevent the cis-isomers from being converted into the trans-isomers during distillation, resulting in easily and efficiently increasing the content of the cis-isomers.

The thus obtained methyl jasmonate mixture contains 20 to 50% of the cis-isomers, namely 10 to 25% of (+) cis-isomer which is the essence of fragrance, and provides a fragrant composition of intense fragrance. It is expected that as the content of the cis-isomers is higher, the intensity of fragrance would be stronger. However, the fragrant composition of the present invention exhibits a strong fragrance than expected. The fragrant composition shows the fragrance degree almost the same as that of the composition containing 80% of the cis-isomers in the total amount of the cis- and trans-isomers. The resulting composition is sufficiently satisfactory as a fragrant composition.

In the case of the content of the cis-isomers is less than 20%, the intensity of fragrance is insufficient. Even though the absolute concentration of the cis-isomers in the fragrant composition is increased, it is difficult to obtain a satisfactory efficiency. Conversely when the content of the cis-isomers exceeds 50% in the total amount of the cis- and trans-isomers, there is no significance in increasing the content because of the reasons described above. Also taking labors required for the operation, etc. into account, it is not economical to increase the content to more than the upper limit.

The fragrant composition of the present invention has jasmine flower-like fragrance and can thus be used as a fragrant ingredient for products such as perfume, lotion, soap, shampoo, food, etc. An amount of the fragrant composition to be formulated varies depending upon fragrance required and method for use, etc. but it is generally controlled to have the fragrant composition in 0.1 to 20 wt % in the product.

When the fragrant composition of the present invention is diluted with a volatile solvent at normal temperature, e.g., a diluting solvent for perfume, lotion, etc., the effect of the present invention described above is more remarkable. That is, where the relative concentration of the cis-isomers to that of trans-isomers in the diluted fragrant composition is constant, the composition containing 20 to 50% of the cis-isomers exhibits the same intensity of fragrance as that containing 80% of the cis-isomers.

Examples of the volatile solvent at normal temperature include alcohols such as ethanol, propyl alcohol, diisopropyl alcohol, hexylene alcohol, etc. and an aqueous solution thereof. Ethanol is especially preferred. A dilution rate may vary depending upon fragrance required, method for use, kind of solvent, etc. and is not generally determined but in general, the dilution rate is in the range of from 0.1 to 20% (parts by weight) of the cis- and trans-isomers in total.

Thus according to the second aspect of the present invention, the fragrant composition which is excellent in jasmine flower-like fragrance as compared to the prior art can be obtained.

Hereafter the present invention is described more specifically by referring to the following examples. In the examples and comparative examples, % is by weight unless otherwise indicated.

EXAMPLE 1

After 20 mg of the metal carbonates shown in Table 1 was mixed with 2.0 g of methyl jasmonate (content of the cis-isomers, 0.6% ; content of the trans-isomers, 99.4%) having purity of 100%, the mixture was stirred at 180° C. for a definite period of time in a nitrogen atmosphere. Without causing side reactions such as decomposition, etc., 2.0 g of methyl jasmonate having purity of 100% was obtained. The content of the cis-isomers is as shown in Table 1.

The content of the cis-isomers (%) is calculated from the peak area values in gas chromatography, in terms of a ratio of the cis-isomers to the total weight of the cis-isomers and the trans-isomers.

TABLE 1

| Run No. | Metal Carbonate | Reaction Time (hr) | Content of Cis-Isomers (%) |
| --- | --- | --- | --- |
| I-1-1 | Sodium carbonate | 5 | 10.8 |
| I-1-2 | Sodium hydrogen carbonate | 5 | 10.6 |
| I-1-3 | Potassium carbonate | 3 | 10.4 |
| I-1-4 | Lithium carbonate | 19 | 10.5 |
| I-1-5 | Calcium carbonate | 19 | 9.0 |
| I-1-6 | Nickel carbonate | 21 | 5.6 |
| I-1-7 | Copper carbonate | 21 | 5.8 |

COMPARATIVE EXAMPLE 1

The same procedures as in Example 1 were repeated except for using no metal carbonate. The content of the cis-isomers in the reaction product was 2.4 (%) after reacting for 19 hours.

The reaction was continued for further 5 hours, whereby coloration was noted and side reactions such as decomposition and the like occurred.

EXAMPLE 2

The procedures were performed in a manner similar to Example 1 except that the metal carbonates shown in Table 2 were used and the reaction temperature and time were changed to 120° C. and 10 hours, respectively. The results are shown in Table 2.

TABLE 2

| Run No. | Metal Carbonate | Rate of Cis-Isomers |
| --- | --- | --- |
| I-2-1 | Sodium carbonate | 9.0 |
| I-2-2 | Potassium carbonate | 9.0 |
| I-2-3 | Sodium hydrogencarbonate | 7.3 |

EXAMPLE 3

The procedures were performed in a manner similar to Example I-1-1 except that 2.0 g of methyl jasmonate (purity, 100%) having the trans-isomers content of 100% was used. Thus, 2.0 g of methyl jasmonate (purity, 100%) showing the cis-isomers content of 10.2% was obtained.

EXAMPLE 4

The procedures were performed in a manner similar to Example I-1-1 except that 2.0 g of methyl dihydrojasmonate (purity, 100%) having the cis-isomers content of 6.7% was used. Thus, 2.0 g of methyl dihydrojasmonate (purity, 100%) showing the cis-isomers content of 12.7% was obtained.

EXAMPLE 5

The procedures were performed in a manner similar to Example 4 except that the reaction temperature was changed to 120° C. Thus, 2.0 g of methyl jasmonate (purity, 100%) showing the cis-isomers content of 12.2% was obtained.

EXAMPLE 6

After 1.0 g of sodium carbonate was added to 100 g of methyl jasmonate (content of the cis-isomers, 0.6% ; content of the trans-isomers, 99.4%) having purity of 100%, the mixture was stirred at the temperature shown in Table 3 for 3 hours. Then, insoluble sodium carbonate was removed by filtration. The concentration of sodium carbonate dissolved in the filtrate is as shown in Table 3. The filtrate was stirred at 180° C. for 13 hours to give 100 g of methyl jasmonate (purity of 100%) having the cis-isomers content of 10.6%. Subsequently, distillation (1 mmHg, boiling point of 122° C.) was performed to purify. Thus, 94 g of methyl jasmonate (purity of 100%) having the content of the cis-isomers shown in Table 3 was obtained (Run Nos. I-3-1 through I-3-3).

The same procedures were also repeated except for performing the filtration. Thus, 94 g of methyl Jasmonate (purity of 100%) was obtained. The content of the cis-isomers is shown in Table 3 (Run No. I-3-4).

TABLE 3

| Run No. | Temperature (°C.) | Concentration of Sodium Carbonate (ppm) | Content of Cis-Isomer (%) |
| --- | --- | --- | --- |
| I-3-1 | 20 | 0.3 | 10.3 |
| I-3-2 | 60 | 0.9 | 10.1 |
| I-3-3 | 120 | 6.9 | 9.9 |
| I-3-4 | 180 | $10^4$ | 8.5 |

From the results shown in Table 3 it is understood that the cis-isomers content in methyl jasmonate obtained by the distillation is reduced as compared to that prior to the distillation but controlling delicately the amount of sodium carbonate to a trace amount, the reduction in the content of the cis-isomers,upon distillation can be prevented (Run Nos. I-3-1 through I-3-3).

EXAMPLE 7

After 1 g of sodium carbonate was mixed with 100 g of methyl jasmonate (content of the cis-isomers, 5%; content of the trans-isomers, 95%) having purity of 100%, the mixture was stirred at 180° C. for 5 hours in a nitrogen atmosphere to give the crude reaction product. The crude reaction product was distilled under reduced pressure to give 98 g of methyl jasmonate (content of the cis-isomers, 10% ; content of the trans-isomers, 90%) having purity of 100%.

Then, methyl jasmonate was distilled under reduced pressure (boiling point of 111° to 112° C., pressures of 0.3 mmHg), using a fractionating tower (packed with SUS316-made filler), which had been previously washed with hot water, to give 25 g of methyl jasmonate (content of the cis-isomers, 20% ; content of the trans-isomers, 80%) having purity of 100%.

The content of the cis-isomers (%) is calculated from the peak area values in gas chromatography, in terms of a ratio of the cis-isomers to the total weight of the cis-isomers and the trans-isomers.

EXAMPLE 8

Methyl jasmonate having the composition shown in Table 4 was diluted with ethanol to prepare 100 g of the diluted fragrant composition. Dilution was performed to have 0.2% of an absolute concentration of the cis-isomers in the diluted composition (Run Nos. II-2-1 through II-2-6). The diluted composition was applied to a fragrant sheet. The sheet was allowed to stand until ethanol evaporated off. Fragrance of the sheet was then evaluated by five (5) panelers (A through E). The evaluation was made by the following 5 levels of fragrant intensity and each evaluation was expressed by points. Comparison was made by the total points.

Very strong fragrance : 4 points
Strong fragrance : 3 points
Medium fragrance : 2 points
Slight fragrance : 1 point
No fragrance : 0 point Further for reference examples, fragrance was also evaluated in a similar manner, with respect to the diluted fragrant composition containing 100% of the trans-isomers and having 2% of an absolute concentration of the trans-isomers (Run No. II-2-7); and the diluted fragrant composition containing 10% of the cis-isomers and having 1% of an absolute concentration of the cis-isomers (Run No. II-2-8).

The results are shown in Table 4.

TABLE 4

| Run No. *1 | Methyl Jasmonate | | Evaluation of Fragrance | | | | | |
|---|---|---|---|---|---|---|---|---|
| | Rate of cis-Isomer (%) | Rate of trans-Isomer (%) | A | B | C | D | E | Total |
| Example: | | | | | | | | |
| II-2-1 | 20 | 80 | 2 | 3 | 3 | 2 | 2 | 12 |
| II-2-2 | 40 | 60 | 2 | 2 | 3 | 3 | 2 | 12 |
| II-2-3 | 50 | 50 | 2 | 2 | 3 | 4 | 2 | 13 |
| Comparative Example: | | | | | | | | |
| II-2-4 | 10 | 90 | 1 | 1 | 1 | 1 | 1 | 5 |
| II-2-5 | 80 | 20 | 3 | 2 | 3 | 2 | 3 | 13 |
| II-2-6 | 100 | 0 | 4 | 4 | 4 | 3 | 4 | 19 |
| Reference Example: | | | | | | | | |
| II-2-7 | 0 | 100 | 0 | 0 | 0 | 0 | 0 | 0 |
| II-2-8 | 10 | 90 | 2 | 2 | 1 | 1 | 2 | 8 |

*1: Methyl jasmonate used in Run Nos. II-2-2 and II-2-3 was synthesized in a manner similar to Example 7. Methyl jasmonate used in Run Nos. II-2-5 to II-2-7 was the product obtained by fractionating the crude reaction product obtained in Example 7 using high performance liquid chromatography and adjusting the resulting cis- and trans-isomers in a desired ratio.

From the results shown in Table 4, it is understood that when the content of the cis-isomers becomes 20% or more, the degree of fragrance becomes strong. Further in the case that the absolute concentration of the cis-isomers in the diluted fragrant composition is the same, the compositions containing 20 to 50% of the cis-isomers (Run Nos. II-2-1 and II-2-3) have almost the same intensity of fragrance as that of the composition containing 80% of the cis-isomers (Run No. II-2-5). On the other hand, the compositions of the present invention (Run Nos. II-2-1 through II-2-3) have stronger fragrance than that having the concentration of 5-fold (Run No. II-2-8). It is also understood that the composition containing 10% of the cis-isomers in the total amount of cis- and trans-isomers has no great improving effect, even though the absolute concentration in the composition is increased.

EXAMPLE 9

After 1 g of sodium carbonate was mixed with 100 g of methyl dihydrojasmonate (content of the cis-isomers, 6% ; content of the trans-isomers, 94%) having purity of 100%, the mixture was stirred at 180° C. for 5 hours in a nitrogen atmosphere to give the crude reaction product, The crude reaction product was distilled under reduced pressure to give 98 g of methyl dihydrojasmonate (content of the cis-isomers, 12% ; content of the trans-isomers, 88%) having purity of 100%.

Then, methyl dihydrojasmonate was distilled under reduced pressure (boiling point of 105° to 107° C., pressures of 0.3 mmHg), using a fractionating tower (packed with SUS316-made filler), which had been previously washed with hot water, to give 30 g of methyl dihydrojasmonate (content of the cis-isomers, 20%; content of the trans-isomers, 80%) having purity of 100%.

EXAMPLE 10

Methyl dihydrojasmonate having the composition shown in Table 5 was diluted with ethanol to prepare 100 g of a diluted fragrant composition. Dilution was performed to have 0.2% of an absolute concentration of the cis-isomers in the diluted composition (Run Nos. II-4-1 through II-4-6). The diluted composition was applied to a fragrant sheet. The sheet was allowed to stand until ethanol evaporated off. Fragrance of the sheet was then evaluated by five (5) panelers (A through E). The evaluation was made by the following 5 levels of fragrant intensity and each evaluation was expressed by pointes. Comparison was made by the total points.

Very strong fragrance : 4 points
Strong fragrance : 3 points
Medium fragrance 2 points
Slight fragrance : 1 point
No fragrance : 0 point Further for reference examples, fragrance was also evaluated in a similar manner, with respect to the diluted fragrant composition containing 100% of the trans-isomers and having 2% of an absolute concentration of the trans-isomers (Run No. II-4-7); and the diluted fragrant composition containing 10% of the cis-isomers and having 1% of an absolute concentration of the cis-isomers (Run No. II-4-8).

The results are shown in Table 5.

TABLE 5

| Run No. *2 | Methyl Dihydrojasmonate | | Evaluation of Fragrance | | | | | |
|---|---|---|---|---|---|---|---|---|
| | Rate of cis-Isomers (%) | Rate of trans-Isomers (%) | A | B | C | D | E | Total |
| Example: | | | | | | | | |
| II-4-1 | 20 | 80 | 3 | 3 | 2 | 2 | 3 | 13 |
| II-4-2 | 40 | 60 | 3 | 2 | 3 | 2 | 3 | 13 |
| II-4-3 | 50 | 50 | 3 | 2 | 3 | 3 | 4 | 15 |
| Comparative Example: | | | | | | | | |
| II-4-4 | 10 | 90 | 1 | 1 | 1 | 1 | 1 | 5 |
| II-4-5 | 80 | 20 | 3 | 2 | 3 | 3 | 4 | 15 |
| II-4-6 | 100 | 0 | 4 | 4 | 4 | 4 | 4 | 20 |
| Reference Example: | | | | | | | | |
| II-4-7 | 0 | 100 | 0 | 0 | 0 | 0 | 0 | 0 |
| II-4-8 | 10 | 90 | 2 | 1 | 1 | 1 | 2 | 7 |

*2: Methyl dihydrojasmonate used in Run Nos. II-4-2 and II-4-3 was synthesized in a manner similar to Example 9. Methyl dihydrojasmonate used in Run Nos. II-4-5 to II-4-7 was the product obtained by fractionating the crude reaction product obtained in Example 9 using high performance liquid chromatography and adjusting the resulting cis- and trans-isomers in a desired ratio.

From the results shown in Table 5, it is understood that when the content of the cis-isomers become 20% or more, the degree of fragrance becomes strong. Further in the case that the absolute concentration of the cis-isomers in the diluted fragrant composition is the same, the compositions containing 20 to 50% of the cis-isomers (Run Nos. II-4-1 and II-4-3) has almost the same intensity of fragrance as that of the composition containing 80% of the cis-isomers (Run No. II-4-5). On the other hand, the compositions of the present invention (Run Nos. II-4-1 through II-4-3) have stronger fragrance than that having the concentration of 5-fold (Run No. II-4-8). It is also understood that the composition containing 10% of the cis-isomers has no great improving effect, even though the absolute concentration of the cis-isomers is increased.

What is claimed is:

1. A fragrant composition consisting essentially of 20 to 50 wt % of the cis-isomers (racemate) of methyl jasmonate or methyl dihydrojasmonate and 80 to 50 wt % of the trans-isomers (racemate) of the same jasmonate, said composition being at about ambient temperature.

2. A fragrant composition according to claim 1 which is obtained by heating the trans-isomers of methyl jasmonate or methyl dihydrojasmonate in the presence of a metal carbonate, then the resulting crude mixture of methyl jasmonate or methyl dihydrojasmonate containing the cis-isomers of methyl jasmonate or methyl dihydrojasmonate, so as to purify the mixture of methyl jasmonate or methyl dihydrojasmonate and then concentrating the resultant by distillation.

3. A fragrant composition of claim 1, which further comprises a volatile solvent at normal temperature.

4. A fragrant composition of claim 3, wherein said volatile solvent at normal temperature is an alcohol or an aqueous solution of alcohol.

5. A fragrant composition of claim 4 wherein the cis- and trans-isomers of methyl jasmonate or methyl dihydrojasmonate are 0.1 to 20 wt % in total.

* * * * *